(12) United States Patent
Andoh et al.

(10) Patent No.: US 8,956,606 B2
(45) Date of Patent: Feb. 17, 2015

(54) MALIGNANT TUMOR CELL SUPPRESSOR PROTEIN, MALIGNANT TUMOR CELL SUPPRESSOR GENE, MALIGANT TUMOR CELL SUPPRESSIVE VIRAL VECTOR, AND KIT USING THE SAME

(75) Inventors: Toshiwo Andoh, Hidaka (JP); Tetsuo Sugahara, Hachioji (JP); Yoshihide Hayashizaki, Yokohami (JP); Yasushi Okazaki, Hidaka (JP)

(73) Assignee: Toshiwo Andoh, Tokyo (JP)

( * ) Notice: Subject to any disclaimer, the term of this patent is extended or adjusted under 35 U.S.C. 154(b) by 1827 days.

(21) Appl. No.: 11/922,933

(22) PCT Filed: Jun. 30, 2006

(86) PCT No.: PCT/JP2006/313145
§ 371 (c)(1),
(2), (4) Date: Nov. 19, 2008

(87) PCT Pub. No.: WO2007/004587
PCT Pub. Date: Nov. 1, 2007

(65) Prior Publication Data
US 2010/0040578 A1  Feb. 18, 2010

(30) Foreign Application Priority Data
Jun. 30, 2005  (JP) .................................. 2005-191789

(51) Int. Cl.
*C12N 15/861* (2006.01)
*C12N 15/85* (2006.01)
*C12N 15/63* (2006.01)
*C12N 5/10* (2006.01)

(52) U.S. Cl.
USPC ....... 424/93.2; 435/320.1; 435/455; 435/325; 424/233.1; 424/93.21; 424/199.1; 424/138.1

(58) Field of Classification Search
None
See application file for complete search history.

(56) References Cited

U.S. PATENT DOCUMENTS 7,745,391 B2 * 6/2010 Mintz et al. ................... 514/19.3
2003/0082722 A1 * 5/2003 Fang ............................. 435/69.1

FOREIGN PATENT DOCUMENTS

WO   WO 2006/110593 A2   10/2006

OTHER PUBLICATIONS

Guo et al, Protein tolerance to random amino acid change, PNAS, 2004, vol. 101 (25), pp. 9205-9210.*
Lesk et al, Prediction of Protein Function from Protein Sequence and Structure, p. 27 and 28, downloaded Sep. 16, 2007.*
Orkin et al., UReport and Recommendations of the Panel to Assess the NIH Investment in Research on Gene Therapy, Issued by the U.S. National Institutes of Health, Bethesda, MD, Dec. 7, 1995.*
Russell, S. J., Replicating Vectors for Gene Therapy of Cancer: Risks, Limitations and Prospects, European J Cancer, 1994, vol. 30A (8), pp. 1165-1171.*
Thomas et al, Progress and Problems With the Use of Viral Vectors for Gene Therapy, Nature, 346 I May 2003, vol. 4, pp. 346-358.*
Adachi J. et al., Database GenBank [online], Accession No. AK037059, <http://www.ncbi.nlm.nih.gov/entrez/viewer.fcgi?26331917:OLD12:2424096> Dec. 5, 2002.
Wu, L. et al., Trends in molecular medicine, 2003, vol. 9, No. 10, pp. 421-429.
Larsson M., et al. J. Biotechnol., 2000, vol. 80, No. 2, pp. 143-157.
Misawa K., et al., Proc. Natl. Acad. Sci. U.S.A., 2000, vol. 97, No. 3062-3066.
Sawasaki T., et al., Proc. Natl. Acad. Sci. U.S.A., 2002, vol. 99, No. 23, pp. 14652-14657.
Magnus Larsson et al.; High-throughput protein expression of cDNAs products as a tool in functional genomics; Journal of Biotechnology, 2000, vol. 80, No. 2, pp. 143-157.
Kazuhide Misawa at al.; A method to identify cDNAs based on localization of green fluorescent protein fusion products; Proc. Natl. Acad. Sci., 2000, vol. 97, No. 7, pp. 3062-3066.
Tatsuya Sawasaki et al.; A cell-free protein synthesis system for high-throughput proteomics; Proc. Nat. Acad. Sci., 2002, vol. 99, No. 23, pp. 4652-4657.

* cited by examiner

*Primary Examiner* — Maria Marvich
(74) *Attorney, Agent, or Firm* — Birch, Stewart, Kolasch & Birch, LLP (57) ABSTRACT

A malignant tumor cell suppressor protein (a) or (b):
(a) a protein comprising an amino acid sequence represented by SEQ ID No. 1; or
(b) a protein comprising an amino acid sequence represented by SEQ ID No. 1, wherein one or more amino acid are deleted, substituted or added in the amino acid sequence set forth in SEQ ID No. 1.

18 Claims, 3 Drawing Sheets

Fig. 1

```
        10         20         30         40         50         60         70         80         90
MKLALLPWIL MLLSTIPGPG FTAGAQGSCS LRCGAQDGLC SCHPTCSGLG TCCEDFLDVC LEILPSSGSM MGGKDFVVQH LKWTDPTDGV
       100        110        120        130        140        150        160        170        180
ICAFKESIQT LGVVDDFYQV HCISPLLYES GVIPFTISMD NGRSFPHAGT WLAAHPYKVS ESEKSQLVNE THWQYYGTSD TRGNLNLTWD
       190        200        210        220        230        240        250        260        270
TSALPTPAVT IELWGYEETG KPYSGNWTSK WSVLVPLATN IPNTGFFTFT PKPASPQVQR WKVGALRISS SRNVPGEKDV RALWTNDHAL
       280        290        300        310        320        330        340        350        360
AWHLGDDFRA DSVAWARAQC LAWEARLEDQL PNFLTELPDC PCTLAQARAD SGRFFTDYGC DIEWGSVCTV HPGAVHCVRS VQRSPRVGSG
       370        380        390        400        410        420        430        440        450
QQCCYTAAGT QLLTSDSTSG STPDRGHDWG APPYATPPRV TGMSHWLYDV ISFYYCCLWA PECPRVMKRR PSSDCRNYAP PRLASAFGDP
       460        470        480        490        500        510        520        530        540
HFVTFDGTSF SFSGNGEVWL LETTLSDLRV QGRAQPGRMP NGTQARGTGL TAVAVQEDNS DVIEVRLAGG SRVLEVLLNQ KVLSFTEQNW
       550        560        570        580        590        600        610        620        630
MDLKGMFLSV AAQDKVSIML SSGAGLEVGV QGPFLSVSIL LPEKFLTHTR GLLGTLNNNP ADDFTLANGQ VLPLNASAQQ VFQFGADWAV
       640        650        660        670        680        690        700        710        720
SNTSSLFTYD SWLLVYQFVY GPKHNPNFKP LFPDETTLSP SQTEDVARLC EGDRFCILDV MSTGSSSVGN ATRIAHQLHQ HRLKSLQPVV
       730        740        750        760        770        780        790        800        810
SCGWLPPPAN GHKEGLRYLE GSVVRFSCNN GVSLVGPESS TCQADGKWSM PTPECQPGRS YTVLLSIIFG GLAIVALISI IYMMLHRRRK
       820
SNMTMWSSQP
```

G5E4T Sequence

TCCGGAGGACAGTACTCCGCTCGGAGGACAGTACTCCGCTCGGAGGACAGT
ACTCCGCTCGGAGGACAGTACTCCGCTCGGAGGACAGTACTCCGACTCTAGA
GGATCCCCAGTCCTATATATACTCGCTCTGCACTTGGCCCTTTTTTACACTGTG
ACTGATTGAGCTGGTGCCGTGTCGAGTGGTGTCTCGAGATCTGCGATCTAAG
TAA

The region indicated by single represents the G5DNA binding site,
while the region indicated by double underline, the E4TATA promoter.

Fig. 4

Induction of SVS-1 with Ad-Gal4Vp2

MALIGNANT TUMOR CELL SUPPRESSOR PROTEIN, MALIGNANT TUMOR CELL SUPPRESSOR GENE, MALIGANT TUMOR CELL SUPPRESSIVE VIRAL VECTOR, AND KIT USING THE SAME

TECHNICAL FIELD

The present invention relates to a malignant tumor cell suppressor protein, a malignant tumor cell suppressor gene, and a recombinant vector for suppressing a malignant tumor cell. More specifically, the present invention relates to a viral vector having anti-tumor activity specific to malignant tumor cells and a kit using the same.

BACKGROUND ART

Human and mouse cDNAs have been studied in projects aimed at elucidating human and mouse genomes. Mouse genomes are very similar to human genomes; genes isolated in mouse can be used directly in studies on human diseases; and mice are generally used as research models for study of human diseases. In particular, studies are comprehensive analytical methods of analyzing the difference in gene expression in different cells by using a mouse cDNA microarray, and the difference in gene expression in organs related various human cancers, i.e. between cancerous tissues and normal tissues. As a result, various new cancer-related genes have been identified. For example, various tumor suppressor genes were identified and analyzed, and proved to be effective in suppressing cancer and thus, useful as a therapeutic target genes (genes such as P53, P16waf-1, Rb, PTEN, TSLC-1, and KAI-1) in preclinical tests (animal tests).

Sequences of a great number of various genes have been determined by comprehensive analysis of the gene sequence of full-length cDNA. However, the functions of most of the genes in the body remain unidentified even now (see, for example, Okazaki, Y., Hayashizaki, Y. et al.: Analysis of the mouse transcriptome based on functional annotation of 60,770 full-length cDNAs Nature 420(6915), 563-573 (2002), Strausberg, R. L. et al.; Generation and initial analysis of more than 15,000 full-length human and mouse cDNA sequences Proc. Natl. Acad. Sci. U.S.A. 99(26), 16899-16903 (2002)).

Gene therapy is currently practiced as one of cancer therapies. However, it is only possible to apply a viral vector only in the region of target cell by the gene therapy, because gene introduction is performed by using a nonproliferating viral vector for safety, and thus, the incorporation efficiency is low, making it difficult to obtain a satisfactory treatment effect.

It is also known that telomerase activity is often raised in cancerated or immortalized cell lines, while the telomerase activity is almost undetectable in normal somatic cells other than germ cells, blood cells, epithelial stem cells and the like.

DISCLOSURE OF INVENTION

An object of the present invention is to provide a viral vector proliferating and being expressed specifically in malignant tumor cells and showing an anti-tumor action, and a kit using the same.

After comprehensive expression analysis aimed at identifying a gene controlling growth, infiltration (invasion) and metastasis of cancer cells, the inventors have found malignant tumor suppressor genes SVS-1 (mouse SVS-1 (mSVS-1) and human SVS-1 (hSVS-1) gene) among the genes identified comprehensive with cDNA arrays and that the gene has a function to inhibit proliferation of malignant tumor cells. The present invention was accomplished, based on the finding, and includes the following aspects:

According to the present invention, there is provided the following means:

(1) A malignant tumor cell suppressor protein (a) or (b):

(a) a protein comprising an amino acid sequence represented by SEQ ID No. 1; or (b) a protein comprising an amino acid sequence represented by SEQ ID No. 1, wherein one or more amino acid are deleted, substituted or added in the amino acid sequence set forth in SEQ ID No. 1.

(2) A malignant tumor cell suppressor gene (c) or (d):

(c) a DNA comprising an nucleotide sequence represented by SEQ ID No. 2; or (d) a DNA comprising an nucleotide sequence represented by SEQ ID No. 2, wherein one or more nucleotide are deleted, substituted or added in the nucleotide sequence set forth in SEQ ID No. 2.

(3) A recombinant vector comprising a gene coding the malignant tumor cell suppressor protein described in the item (1) downstream of a promoter sequence to which a transcription factor binds.

(4) A recombinant adenoviral vector comprising a gene coding the transcription factor described in the item (3) downstream of a telomerase promoter.

(5) A viral vector kit for suppressing a malignant tumor cell, comprising the recombinant vector described in the item (3) and the recombinant adenoviral vector described in the item (4).

(6) A recombinant adenoviral vector comprising a gene coding the malignant tumor cell suppressor protein described in the item (1) downstream of a telomerase promoter; and (7) A recombinant adenoviral vector comprising a gene coding a transcription factor downstream of a telomerase promoter, and a gene coding the malignant tumor cell suppressor protein described in the item (1) downstream of a promoter sequence to which the transcription factor binds.

Other and further features and advantages of the invention will appear more fully from the following description, appropriately referring to the accompanying drawings.

BEST MODE FOR CARRYING OUT THE INVENTION

Hereinafter, the present invention will be described in detail.

A method of obtaining a malignant tumor cell suppressor gene such as the gene according to the present invention will be described first. Screening of a malignant tumor cell suppressor gene may be performed, for example, by mouse cDNA microarray method.

Mouse genomes are very similar to human genomes, and thus, genes isolated in mouse can be used directly as they are for studies on human diseases (see, for example, Okazaki, Y., Hayashizaki, Y. et al.: Analysis of the mouse transcriptome based on functional annotation of 60,770 full-length cDNAs Nature 420 (6915), 563-573 (2002)).

The cDNA microarray method can be performed according the method described, for example, in Yoshihide Hayashizaki supervised, Koji Okazaki Ed., "Practical DNA Microarray Manual for reliable production of data" (Yodosha), Mark Schena Ed., Ikunoshin Kato supervised and translated "DNA microarray" (Maruzen), and the like.

For example, it is possible to analyze the difference in gene expression between mouse normal fibroblast NIH3T3 and a transformant (TF, cancerated) Ki-3T3 cell with activated oncogene v-K-ras, by using a microarray carrying 20,000 (20K) mouse cDNAs. As will be described below in Examples, in the cancerated cell Ki-3T3, 433 genes expressing the protein in a greater amount, by twice or more than in the parent strain NIH3T3 are identified, while 313 genes expressing in an amount of ½ or less, as expression is inhibited, are identified nucleotide.

In addition, it is possible to estimate the functions of the proteins coding the genes above by functional domain search, for example, NCBI Conserved Domain Search www.ncbi.nlm.nih.gov/Structure/cdd/cdd.shtml), based on the translation regions in the genes with lowered expression. In this way, it is possible to identify multiple genes that would have anticancer activity.

For example, it is possible to obtain the gene represented by SEQ ID No. 2 (hereinafter, referred to simply as SVS-1 gene) coding the malignant tumor cell suppressor protein according to the present invention (SEQ ID No. 1; hereinafter referred to simply as SVS-1 protein).

Figure 1:
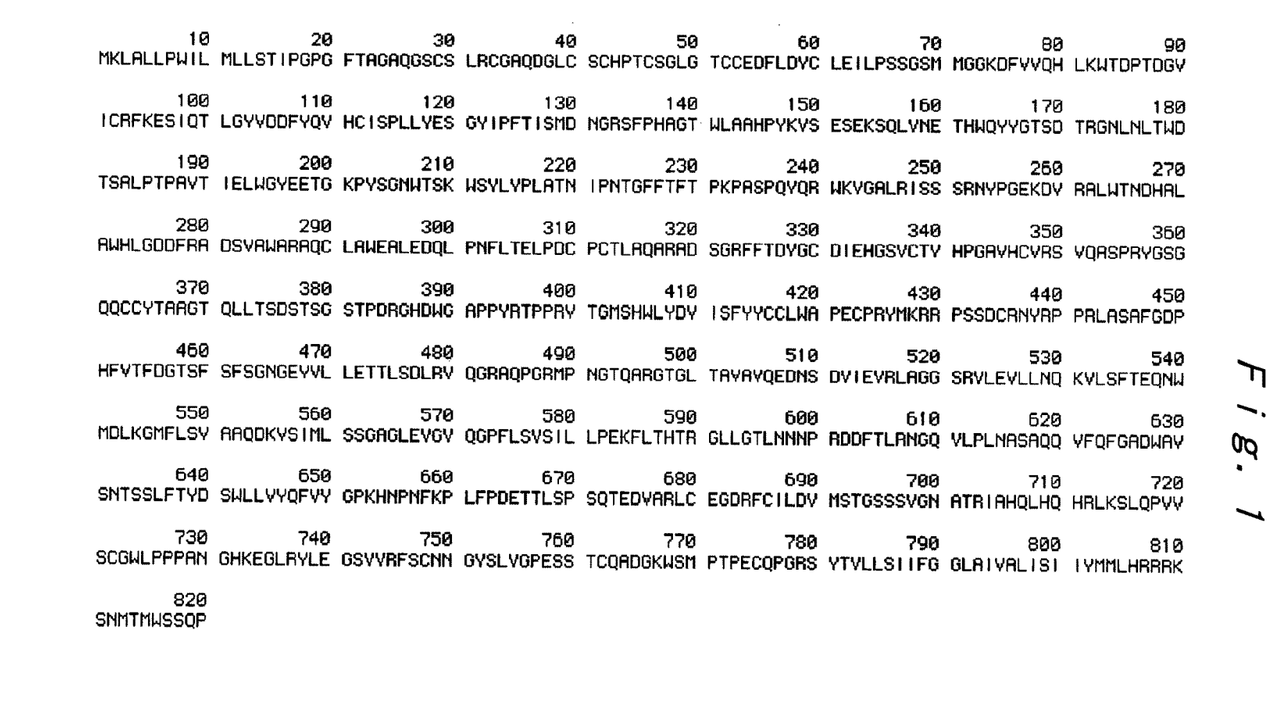
FIG. 1 is a chart showing an amino acid sequence (SEQ ID No. 1) of a malignant tumor cell suppressor protein.

FIG. 1 is a chart showing the amino acid sequence (SEQ ID No. 1) of the malignant tumor cell suppressor protein.

Figure 2:
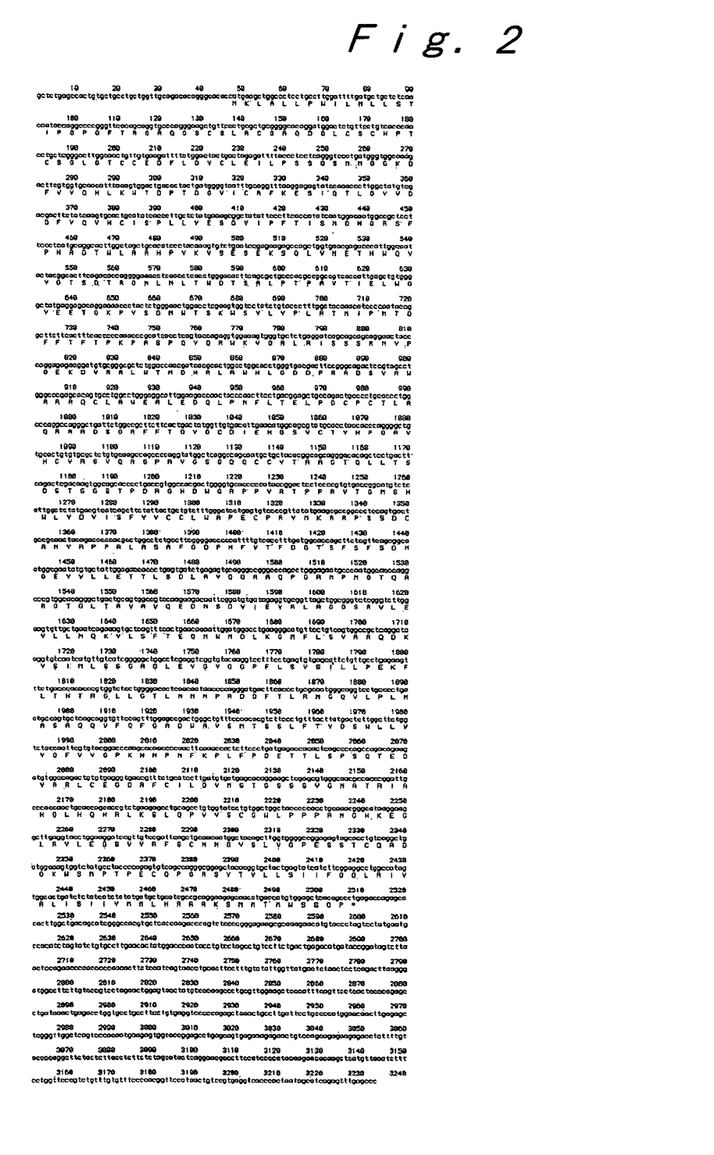
FIG. 2 is a chart showing the relationship between a nucleotide sequence (SEQ ID No. 2) of the malignant tumor cell suppressor gene and the amino acid sequence (SEQ ID No. 1) shown in FIG. 1.

FIG. 2 is a chart showing the correlation between the nucleotide sequence (SEQ ID No. 2) of the malignant tumor cell suppressor gene and the amino acid sequence (SEQ ID No. 1) shown in FIG. 1.

Hereinafter, a method of constructing a vector for introduction of the malignant tumor cell suppressor gene into malignant tumor cell will be described.

Because most cancer cells have telomerase activity, the viral vector according to the present invention, which contains a gene having a telomerase promoter incorporated, characteristically kills malignant tumor cells specifically.

The present invention also provides a viral vector kit for suppressing malignant tumor cells, having a recombinant vector for establishing a tumor cell line stably transfected with the SVS-1 gene and an adenoviral vector containing the polynucleotide coding a fusion transcription factor (Gal4VP2) (SEQ ID No. 3). In the kit, the recombinant vector for establishing a tumor cell line stably transfected with the SVS-1 gene and the adenoviral vector containing the polynucleotide coding the fused transcription factor (Gal4VP2) may or may not be mixed with each other. When the kit is a mixture, the component ratio is not particularly limited, but preferably 1:1.

A recombinant vector for establishing a tumor cell line stably transfected with the SVS-1 gene is preferably a recombinant vector having a gene coding the malignant tumor cell suppressor protein (SEQ ID No. 1) downstream of a promoter sequence (G5E4T) to which the fused transcription factor (Gal4VP2) binds.

The host vector used is preferably a plasmid vector pG5 (the vector provided by Prof. L. Wu (University of California at Los Angels, Department of Urology, School of Medicine) (see, for example, the vector described in L. Zhang et al., Molec. Therapy 5 (3): 223-232, 2002)).

Figure 3:
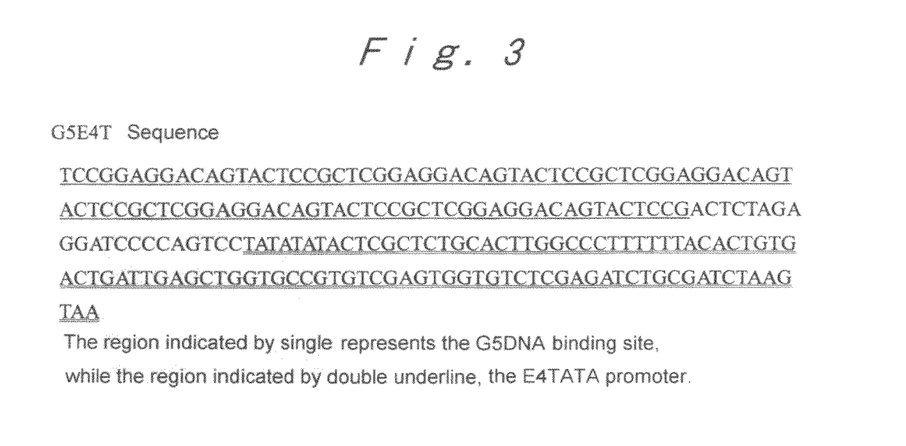
FIG. 3 is a chart showing a G5E4T sequence (SEQ ID No. 4).

FIG. 3 is a chart showing the promoter sequence (G5E4T) (SEQ ID No. 4). As obvious from FIG. 3, the promoter sequence (G5E4T) has a G5 DNA-binding site and an E4TATA promoter.

By binding a Flag tag gene (SEQ ID No. 5) to the gene coding the malignant tumor cell suppressor protein (SEQ ID No. 1) as shown in SEQ ID No. 6, it becomes possible to identify expression of the malignant tumor cell suppressor protein with an anti-FLAG antibody.

By introducing a vector having a G418-resistant gene (e.g., a pcDNA3.1v5his(Neo) vector; manufactured by Invitrogen) additionally, it becomes also possible to select the tumor cell clone stably transfected with the SVS-1 gene by the G418 resistance.

The fusion transcription factor (Gal4VP2)-expressing adenoviral vector for inductive expression of the SVS-1 gene in the stable transfected tumor cell (hereinafter, referred to simply as Ad-Gal4VP2 virus) can be prepared according to the procedures described, for example, in M. Lyer et al., Proc. Nat. Acad. Sci. 98: 14595-14600, 2002; L. Zhang et al., Molec. Therapy 5(3): 223-232, 2002; J. Y. Adams et al., Nature Medicine 8(8): 891-896, 2002; and L. Wu et al., Trends in Molec. Medicine 9(10): 421-429, 2003.

Specifically, the Gal4VP2 gene (SEQ ID No. 3) is first introduced into the restriction enzyme XhoI-XbaI site downstream of a CMV promoter of pShuttle-CMV in an adenoviral vector kit (AdEasy Kit, manufactured by Stratagene). The construct pShuttle-CMV-Gal4VP2 is transformed into competent *E. coli* strain BJ5183-AD1 (manufactured by Stratagene). In the competent *E. coli* cell, recombination is occurred between the adenovirus genome incorporated into the competent *E. coli* and the pShuttle-CMV-Gal4VP2, and thereby obtaining an adenoviral vector DNA constitutively expressing Gal4VP2. It is possible to prepare a desired Gal4VP2-expressing adenoviral vector, by preparing the adenoviral vector DNA from the competent cells and introducing the DNA into a human renal cell line HEK293 which express the adenovirus EIA gene.

In particular, it is also possible to prepare a Gal4VP2-expressing adenoviral vector containing hTERT promoter for specific expression in cancer cells, by the similar manner.

Specifically, the polynucleotide encoding Gal4VP2 (SEQ ID No. 3) is cleaved with restriction enzymes Hind III and Xba I from pcDNA3-Gal4VP2 and inserted into a shuttle-plasmid (pShuttle), which is previously cleaved at the same restriction enzyme sites with Hind III and Xba I, to give a pShuttle-Gal4VP2. Subsequently, a vector pGL3328 which is constructed by being inserted the hTERT promoter into the restriction enzymes sites Mlu I and Bgl II of the pGL-basic (manufactured by Promega) (the vector pGL3328 provided by Dr. Satoru Kyo, Graduate School of Medical Science, Kanazawa University; see, for example, Takakura et al., Cloning of human telomerase catalytic subunit (hTERT) gene promoter and identification of proximal core promoter sequences essential for transcriptional activation in immortalized and cancer cells. Cancer Res. 59: 551-557, 1999) is cleaved with Pvu II and Bgl II, separating the core region of the hTERT promoter, which is further blunt-ended, to give the hTERT fragment. The pShuttle-Gal4VP2 is digested with Bgl II and blunt-ended. The blunt-ended hTERT fragment is inserted into and ligated with the pShuttle-Gal4VP2, to give a vector pShuttle-hTERT-Gal4VP2. Because there may be clones different in the direction of hTERT fragment, only the DNA having the hTERT fragment inserted in the desired direction may be selected by examining fragments generated by restriction enzyme processing. It is possible in this way to prepare the vector pShuttle-hTERT-Gal4VP2. The pShuttle-hTERT-Gal4VP2 is incorporated into competent *E. coli* strain BJ5183-AD1 (manufactured by Stratagene), and then transformed. In the *E. coli* cells, recombination is occurred between the adenovirus genome previously present in the competent *E. coli* and the introduced pShuttle-hTERT-Gal4VP2, constructing an adenoviral vector DNA expressing Gal4VP2 specifically in cancer cells.

It is possible to prepare a Gal4VP2-expressing adenoviral vector containing hTERT promoter for specific expression in cancer cells by preparing the adenoviral vector DNA from the competent *E. coli* and introducing the DNA into a human renal cell line HEK293.

The fusion transcription factor (Gal4VP2) is a composite transcription factor containing the DNA-binding domain of the transcription factor Gal4 and the transcription-activating domain VP2 of the HSV-virus transcription factor VP16, which are fused for specific binding to the synthetic promoter G5E4T and thus inductive expression of the downstream genes and also for improving the transcription efficiency drastically by activating the desired gene by "two-step transcription activation method (TSTA method)".

The fusion transcription factor (Gal4VP2)-expressing adenoviral vector according to the present invention has a human telomerase promoter upstream of the fusion transcription factor (Gal4VP2), because transcription of such a vector is accelerated in the malignant tumor cells having telomerase activity. The promoter is not particularly restricted, for example in its kind, if it is a human telomerase promoter, but preferably hTERT.

The present invention also provides a recombinant adenoviral vector containing a gene coding the malignant tumor cell suppressor protein (SEQ ID No. 1) downstream of a telomerase promoter.

It is more preferably a recombinant adenoviral vector containing a gene coding a transcription factor downstream of a telomerase promoter; and a gene coding the malignant tumor cell suppressor protein downstream of a promoter sequence to which the transcription factor bind.

The virus for use in the present invention is not particularly limited, but preferably an adenovirus, from the points of safety and others. Among adenoviruses, type 5 adenoviruses are particularly preferable, from the points of convenience in handling and others.

The viral vector according to the present invention is a very safe remedy, because of considering extremely less probable to cause adverse reactions, for the following reasons: (1) normal somatic cells have almost no telomerase activity, and the viral vector according to the present invention is less infectious to floating cells such as hematopoietic cell; (2) the viral vector according to the present invention characteristically amplifies expression of a gene downstream of the promoter sequence (G5E4T) as it is induced by the transcription factor Gal4VP2, and thus may be used at a concentration far lower than that of non-induced viruses commonly used in gene therapy; and (3) even when the viral vector according to the present invention is administered in excess, an antiviral action by the immunoreaction which the body naturally has can act on the viral vector.

As described above, the malignant tumor cell suppressor gene according to the present invention can be effectively used in specific inhibition of malignant tumor cells.

Hereinafter, amplification of expression of SVS-1 gene and increase in anti-malignant tumor activity by co-infection to non-proliferating recombinant adenovirus containing SVS-1 gene and restricted-proliferation adenovirus, will be described.

It is known that the non-proliferating virus proliferates in cancer cells and amplifies the gene by co-infection with a restricted-proliferation adenovirus (growing only in cancer cells), consequently leading to drastic increase in expression of the recombinant gene and also in cellular action (see, for example, Sunamura M, Oonuma M, Motoi F, Abe, H, Saitoh Y, Hoshida T, Ottomo S, Hori A and Matsuno S: Gene therapy for pancreatic cancer targeting the genomic alterations of tumor suppressor genes using replication-selective oncolytic adenovirus. Hum Cell. 15:138-150, 2002, Nagayama Y, Nakao K, Mizuguchi H, Hayakawa T and Niwa M: Enhanced antitumor effect of combined replicative adenovirus and non-replicative adenovirus expressing interleukin-12 in an immunocompetent mouse model. Gene Ther. 10:1400-1403, 2003).

Thus, it appears that co-infection of the viral vector according to the present invention and a restricted-proliferation adenovirus, such as AxEIAdB, leads to drastic increase in expression of the SVS-1 gene in malignant tumors and to drastic increase in antitumor activity.

Hereinafter, application of the viral vector according to the present invention will be described.

The viral vector according to the present invention can be used as a vector for anti-malignant tumor. For example, it can be used not only for treatment of a cancer, but also for prevention of recurrence after operation and inhibition and/or prevention of its metastasis.

The kind of the cancers to which the viral vector according to the present invention is applicable include any kinds of cancers. Particularly, it is effective against cancer including solid cancers of stomach, colon, lung, liver, prostate, pancreas, esophagus, bladder, gallbladder and bile duct, breast, uterus, thyroid, ovary and others.

The viral vector according to the present invention may be applied directly to affected regions as it is, and administered into the body (desired cell or organ) by any known methods such as intravenous, intramuscular, intraperitoneal, or subcutaneous injection, inhalation via nasal cavity, oral cavity or lung, oral administration, and application as suppository or an external preparation.

The viral vector according to the present invention that is incorporated or infected into the body, i.e., malignant tumor cells, proliferates in the cells, ultimately killing the cells. It is thus possible to treat cancer and inhibit growth and metastasis of the malignant tumor.

After processing for easier handling for example by freezing, the viral vector may be used as a pharmaceutical composition, as it is or as it is mixed with additional known pharmaceutically acceptable carriers, such as diluent, filler, binder, and lubricant, and other known additives (including buffer agent, isotonic agent, chelating agent, colorant, stabilizer, flavoring agent, seasoning agent, sweetener, and the like).

The viral vector according to the present invention can be administered orally in the shape of tablet, capsule, powder, granule, pill, liquid, syrup or the like; or parenterally in the shape of injection, external preparation, suppository, ophthalmic solution or the like. It is preferably, for example, local injection such as intramuscular and intraperitoneal injection, or an intravenous injection.

The dosage is selected properly according to the kind of active ingredient, administration route, patient, patient age, body weight, gender, symptom, and other conditions, but the dosage per day is normally approximately $1 \times 10^7$ to $1 \times 10^{12}$ PFU, preferably approximately $1\times10^8$ to $1\times10^{11}$ PFU, as the content of active ingredient viral vector according to the present invention, and the preparation may be administered once a day or in portions as divided.

It is also possible to control the immunoreaction of the body and make the viral infection easier, by using a known immunosuppressive agent or the like, together with the viral vector according to the present invention.

It is further possible to use at least one anticancer drug selected from the group consisting of non-proliferating viruses used in conventional gene therapy, such as those containing p53 gene; known anticancer drugs; and radiation ray; in combination the viral vector according to the present invention.

Hereinafter, an antibody binding specifically to the protein according to the present invention will be described.

Any known common method may be used in preparing the antibody binding specifically to the protein according to the present invention. A polypeptide having high antigenicity may be selected from any sequence favorable as the epitope (antigenic determinant) according to a known method, and may be used as antigen. Commercially available software, for example, Epitope Adviser (manufactured by Fujitsu Kyushu System Engineering) may be used in selecting the epitope.

The SVS-1 protein according to the present invention may be used as it is the polypeptide used as antigen. The antigen polypeptide may be processed into a preparation such as a proper solution and the like according to a known method; and used for immunization of mammals such as rabbit, mouse and rat. It is preferable that the antigen peptide is used in immunization as a conjugate with a suitable carrier protein or in combination for example with an adjuvant, for improvement in reliability and in the antibody titer.

The antigen administration route during immunization is not particularly limited, and the preparation may be administered via any route, for example, subcutaneously, intraperitoneally, intravenously, or intramuscularly. Specifically, for example, a method of administering the antigen polypeptide to BALB/c mice several times at an interval of several days to several weeks is used. The dosage of the antigen is preferably approximately 0.3 to 0.5 mg/once when the antigen is a polypeptide, and may be modified properly according to the kind of animal immunized.

After immunization, increase of antibody titer is measured by occasional blood sampling and subsequent analysis thereof, for example, by solid phase enzyme immunoassay (hereinafter, referred to as "ELISA method") or Western blotting; and then, blood is collected from the animal having a sufficiently higher antibody titer. Further, the resultant can be processed by a method appropriately used in antibody preparation to give a polyclonal antibody. Specifically, the method includes a method of obtaining a purified antibody by purifying antibody component from the serum according to a known method. The antibody component can be purified, for example, by salting out, ion-exchange chromatography, affinity chromatography, or the like.

It is also possible to prepare the monoclonal antibody by using a hybridoma prepared by fusion of the spleen cell of the animal and a myeloma cell according to a known method (Milstein, et al., Nature, 256, 495 (1975)).

When a human-derived protein is obtained as the malignant tumor cell suppressor protein according to the present invention, it is possible to prepare a human antibody by immunizing a severe-combined-immune-deficiency (SCID) mouse, to which human peripheral-blood lymph cells are previously transplanted, with the polypeptide or part of the peptide as an antigen, similarly to the method described above; and preparing a hybridoma between the antibody production cell of the immunized animal and a human myeloma cell (Mosier, D. E., et al. Nature, 335, 256-259 (1988): Duchosal, M. A., et al., Nature, 355, 258-262 (1992)).

Further, it is possible to prepare the human antibody in a greater amount, by extracting the RNA from the human antibody-producing hybridoma thus obtained; cloning a gene coding a desired human antibody into a suitable vector; and introducing and amplifying the vector in a suitable host. In the case of an antibody less easily binding to the antigen, it is possible to raise the binding efficiency by using an evolutionary engineering method known in the art. It is possible to prepare the partial fragment such as a monovalent antibody, for example, by cleaving the Fab and Fc regions with papain and the like, and collecting the Fab region by using an affinity column and the like.

The antibody thus obtained that binds specifically to the malignant tumor cell suppressor protein according to the present invention can be used in detection of the malignant tumor cell suppressor protein according to the present invention specifically, because it binds to the protein. In this case, it is possible to detect the protein quantitatively by any secondary antibody detection method.

The protein according to the present invention having a sequence represented by SEQ ID No. 1 has malignant tumor-suppressing action.

The malignant tumor cell suppressor gene according to the present invention would be useful in development of pharmaceutical compositions for treatment of cancer (viral vector, drug development, etc.).

The viral vector and the kit using the same according to the present invention have an action to inhibit growth of malignant tumor cells specifically.

EXAMPLES

The present invention will be described in more detail based on examples given below, but the invention is not meant to be limited by these.

(1) Screening for Malignant Tumor Cell Suppressor Genes with Mouse cDNA Microarray First, the difference in gene expression between the mouse normal fibroblast NIH3T3 and the transformant Ki-3T3 cell transformed with activated oncogene v-K-ras was analyzed by using a microarray carrying 20,000 (20K) mouse cDNAs. As a result, in the cancerated cell Ki-3T3, 433 genes that are expressed in an amount of twice or more, larger than in the parent strain NIH3T3, and 313 genes that are expressed in an amount of ½ or less, lower than in the parent strain, were identified.

(2) Functional Domain Search

Among the above genes of which expression is inhibited, a few genes considered to have possibly anticancer activity were identified by functional domain search based on the proteins coded by the genes. Then, a SVS-1 gene (SEQ ID No. 2) was obtained and a protein translation region of SVS-1 gene was subjected to domain search by using the NCBI Conserved Domain Search (www.ncbi.nlm.nih.gov/Structure/cdd/cdd.shtml).

The domains predicted by the domain search are shown in the following Table 1.

TABLE 1

25th to 62nd amino acid region

SO. somatomedin B-like domains; the somatomedin-B, which is a peptide obtained by protease digestion of vitronectin, is a hormone-dependent serum growth factor having protease-inhibiting activity.
282nd to 430th amino acid region
AMOP. An adhesion-related domain present in MUC4 and other proteins.
435th to 609th amino acid region VWD. von Willebrand factor (vWF) type D domain: the von Willebrand factor includes several type D domains: D1 and D2 domains are present in N-terminal protected peptides, while the other D domains are demanded for multimerization.
722nd to 776th amino acid region CCP. A domain abundant in complement-controlling proteins; SUSHI repeat; Short complement-like repeat (SCR); the complement-controlling protein (CCP) modules (SCR repeats also known as short common repeats or SUSHI repeats) contain approximately 60 amino acid residues, and are fixed in some proteins of complement system. Typically, two to four modules contribute to the binding sites, and the direction of the modules relative to each other is essential for function.
722nd to 775th amino acid region CCP. A domain abundant in complement-controlling proteins; SUSHI repeat; Short complement-like repeat (SCR); the complement-controlling protein (CCP) modules (SCR repeats also known as short common repeats or SUSHI repeats) contain approximately 60 amino acid residues, and are fixed in some proteins of complement system. The missense mutation in the 7th CCP domain leads to deficiency of the b subunit of factor XIII.
722nd to 775th amino acid region Sushi. Sushi domain (SCR repeat).

As obvious from Table 1, the SVS-1 protein has a sushi domain, which is present in a known tumor suppressor gene drs, and also other sushi (CCP, SCR) domains, an AMOP domain, membrane penetration regions and others. As a result, it is presumed that SVS-1 protein is a membrane protein involved in cell adhesion and the like. It is also suggested that the SVS-1 protein has a malignant tumor-suppressing function, because of the fact that many proteins present in the cell membrane and involved in cell adhesion have cancer-suppressing action. As will be described below in "(6) Malignant tumor-suppressing test", the SVS-1 protein is present locally in the cell membrane and a protein involved in cell adhesion and the like, which also supported the suggestion.

(3) Establishment of Stable Transfected Cell Line with SVS-1 Gene (HT/SVS-1 and HeLa/SVS-1)

First, the SVS-1 gene (SEQ ID No. 6) directly connected to a Flag tag gene (SEQ ID No. 5) was inserted to the restriction enzyme Xba I site of a plasmid vector pG5 (vector provided by Prof. L. Wu, University of California at Los Angels, Department of Urology School of Medicine, see, for example, L. Zhang et al., Molec. Therapy 5(3): 223-232, 2002) downstream of the promoter sequence (G5E4T) (SEQ ID No. 4) which is recognized and bound by a fusion transcription factor (Gal4VP2), to give a plasmid vector pG5-Flag-svs1.

Then, the pG5-Flag-svs1 vector and pcDNA3.1v5his(Neo) vector having a G418-resistant gene (manufactured by Invitrogen) are co-introduced into a cancer cell HT1080 (fibrosarcoma) and HeLa cell (uterine cervical cancer) respectively by lipofection. After selection with G418 resistance over two weeks, tumor cell clones stably transfected with SVS-1 gene were obtained. One out of four cloned HT1080 cells and two out of 24 cloned HeLa cells were expression-inducible strains.

(4) Construction of Fusion Transcription Factor Expression Vector

For induced expression of the SVS-1 gene in the stable transfected tumor cell, a fusion transcription factor (Gal4VP2)-expressing adenoviral vector (Ad-Gal4VP2 virus) was prepared according to the method described, for example, in M. Lyer et al., Proc. Nat. Acad. Sci. 98: 14595-14600, 2002, L. Zhang et al., Molec. Therapy 5(3): 223-232, 2002, J. Y. Adams et al., Nature Medicine 8(8): 891-896, 2002, or L. Wu et al., Trends in Molec. Medicine 9(10): 421-429, 2003.

Specifically, the polynucleotide Gal4VP2 (SEQ ID No. 3) was prepared by cleavage of pcDNA3-Gal4VP2 with Hind III and Xba I and inserted into a vector obtained by cleavage of pShuttle with the same restriction enzymes Hind III and Xba I (pShuttle-Gal4VP2). Further, a vector pGL3328 containing a hTERT promoter in the restriction enzyme Mlu I-Bgl II site of pGL-basic (manufactured by Promega) (provided by Dr. Satoru Kyo, Graduate School of Medical Science, Kanazawa University) was cleaved with Pvu II and Bgl II, separating the core region of the hTERT promoter, which was then blunt-ended (hTERT). pShuttle-Gal4VP2 was digested with Bgl II and blunt-ended. The blunt-ended hTERT fragment was inserted therein and ligated, to give a vector pShuttle-hTERT-Gal4VP2. Because the hTERT fragment may be inserted in both directions, a DNA having the hTERT in the desired direction was selected, based on the fragments obtained by restriction enzyme treatment, to give pShuttle-hTERT-Gal4VP2 (yield: 10 μg). The vector pShuttle-hTERT-Gal4VP was then introduced into competent E. coli BJ5183-AD1 (manufactured by Stratagene) ($1 \times 10^{10}$ cells) and the resultant incubated in a LB agar medium at 37° C. overnight, allowing transformation. An adenoviral vector DNA, which express Gal4VP2 specifically in cancer cells, was constructed in E. coli cell by recombination of the adenovirus genome previously present in the competent E. coli with the introduced vector pShuttle-hTERT-Gal4VP2.

The adenoviral vector DNA was prepared from E. coli and introduced into a human renal cell line HEK293, to give a Gal4VP2-expressing adenoviral vector containing the hTERT promoter for specific expression in cancer cells (yield: $1 \times 10^{13}$ PFU).

(5) Analysis of Inductive Expression of SVS-1 Gene
(5-1) The SVS-1-transfected cell line (HT/SVS-1 or HeLa/SVS-1) was infected with the Ad-Gal4VP2 virus, allowing inductive expression of the SVS-1 gene. The culture condition for inductive expression is shown in Table 2.

TABLE 2

| 37° C., 48 hours | Quantity |
| --- | --- |
| Ad-Gal4VP2 virus | 10 moi |
| SVS-1-transfected strain (HT/SVS-1 or HeLa/SVS-1) | 100,000 moi |
| DMEM (Dulbecco-Modified Eagle Medium) | 1 ml/12 well plates |
| Other component | FBS 10% |

Here, moi represents multiplicity of infection, while FBS, fetal bovine serum.

(5-2) For confirmation of expression in comparison with a mock (control cell infected with an empty virus), expression induction by Ad-Gal4VP2 virus was studied under microscope by an immunofluorescent method of using an anti-FLAG antibody.

First, observation of the cancer cell HT1080 (magnification: 200 times) showed that both of the mock and the Ad-Gal4VP2 virus-infected cell were dyed in processing by Hoechst dyeing method (dyeing of live cell nucleus). However, in observation by an immunofluorescence method of using an anti-FLAG antibody (magnification: 200 times), the mock cell was not fluorescent, while the Ad-Gal4VP2 virus-infected cell was fluorescent.

Then, in observation of the HeLa cell (magnification: 400 times), both of the mock cell and the Ad-Gal4VP2 virus-infected cell were dyed by the Hoechst dyeing method (dyeing of live cell nucleus). However, in observation by the immunofluorescence method of using an anti-FLAG antibody (magnification: 400 times), the mock cell was not fluorescent, while the Ad-Gal4VP2 virus-infected cell was fluorescent.

The results indicate that the FLAG-tagged SVS-1 protein is expressed inductively in the Ad-Gal4VP2 virus-infected cell.

(5-3) Inductive expression by the Ad-Gal4VP2 virus was analyzed by Western blotting of using a FLAG antibody (α FLAG). Results are shown in FIG. 4.

Figure 4:
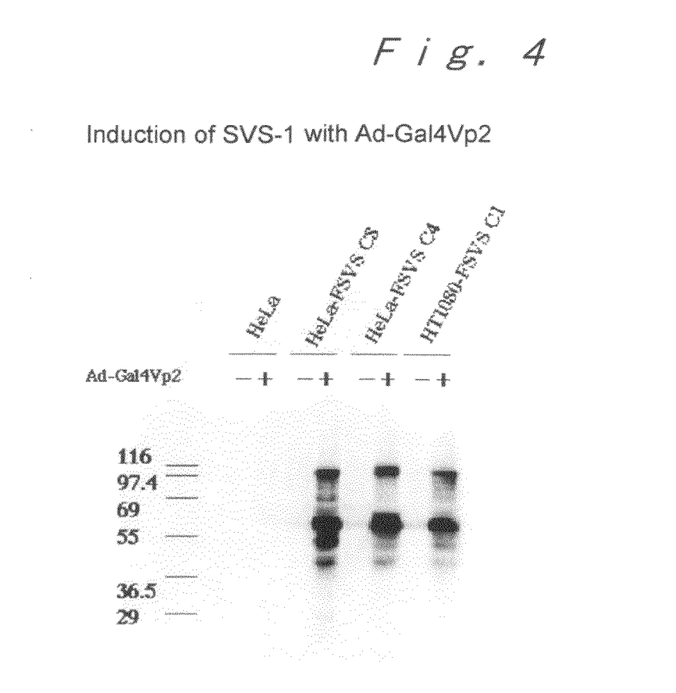
FIG. 4 is a chart showing a result of Western blotting by using a FLAG antibody (α FLAG).

As obvious from FIG. 4, a band of approximately 100 kDa derived from the full-length SVS-1 protein and a band of approximately 60 kDa derived from a processed fragment were found only in the Ad-Gal4VP2 virus-infected cell. The results indicate that there is no expression of the SVS-1 protein without infection with the Ad-Gal4VP2 virus.

(6) Test for Suppressing Malignant Tumor Cell

First, breakdown of the tumor cytoskeleton and subsequent sphericalization of the cell by expression of the SVS-1 gene were studied.

(a) When the SVS-1 cDNA was transfected to a mouse normal fibroblast NIH3T3, microfilaments (actin fibers) in the cytoskeleton disappeared and the cell sphericalized.

(b) Microscopic observation by using a phase-contrast microscope and using an orange fluorescent-labeled SVS-1 protein (magnification 400%) showed that most of HeLa cells sphericalized, forming agglomerates (aggregation), when the SVS-1 was inductively expressed. In the control study by using Ad/GFP (Green Fluorescent Protein), the infected and inductively-expressing cell did not show such a phenomenon (in phase contrast and green fluorescent microscopic observation (magnification: 400%)).

The results above (a) and (b) show that it is possible to act on the cytoskeleton breakdown of malignant tumor cells by inductive expression of the SVS-1 gene therein.

In addition, it seems to be possible to reduce the infiltration or metastatic activity of the malignant tumor cell, by inductive expression of the SVS-1 protein.

Specifically, confocal micrographic image observation (magnification: 800%) revealed that the SVS-1 protein was expressed on the intracellular structure (endoplasmic reticulum) and the cell membrane in cells with increased cell membrane permeability by treatment with TritonX100, but on the external surface of the cell when it is not treated with TritonX100 (the antibody did not penetrate into the cell, allowing dyeing the antigen present outside the cell surface). The sphericalization of cell shape and the cytoskeleton breakdown shown in (a) and (b) above, suggest that the inductive expression is effective in inhibiting infiltration and metastasis of the malignant tumor cell in the body. The suggestion is made, based on the fact that the properties of SVS-1 shown above, such as the intracellular distribution and agglomerate formation, are common to those of the "TSLC-1" gene which was identified as a cancer metastasis-suppressing gene (see, for example, study by groups in National Cancer Center and Univ. Tokyo, J. Biol. Chem. 277: 31014-31019, 2002).

As described above, it is possible to suppress malignant tumor cells by inductive expression of the protein according to the present invention having a sequence represented by SEQ ID No. 1.

Because the above tests were performed by using a cancer cell HT1080 (fibrosarcoma) and HeLa cell (uterine cervical cancer), it is also obvious that it is possible to express the SVS-1 gene inductively, specifically in malignant tumor cells in animal body, and to breakdown the cytoskeleton of the malignant tumor cell.

INDUSTRIAL APPLICABILITY

The malignant tumor cell suppressor protein, the malignant tumor cell suppressor gene, the malignant tumor cell-suppressing viral vector and the kit using the same according to the present invention can be used preferably for specific suppression of malignant tumor cells.

Having described our invention as related to the present embodiments, it is our intention that the invention not be limited by any of the details of the description, unless otherwise specified, but rather be construed broadly within its spirit and scope as set out in the accompanying claims.

The invention claimed is:

1. A viral vector kit, comprising:

a recombinant vector comprising a gene coding for a protein selected from the group consisting of (a) a protein comprising the amino acid sequence of SEQ ID NO: 1; and (b) a protein comprising the amino acid sequence of SEQ ID NO: 1, wherein one amino acid is deleted, substituted, or inserted in the amino acid sequence set forth in SEQ ID NO: 1 and wherein the gene is downstream of a promoter sequence to which a transcription factor binds; and a recombinant adenoviral vector comprising a second gene coding for the transcription factor, wherein the second gene is under control of a telomerase promoter.

2. The viral vector kit according to claim 1, wherein the recombinant vector comprises the gene coding for protein (a).

3. A recombinant adenoviral vector comprising a gene coding for a protein selected from the group consisting of (a) a protein comprising the amino acid sequence of SEQ ID NO: 1; and (b) a protein comprising the amino acid sequence of SEQ ID NO: 1, wherein one amino acid is deleted, substituted, or inserted in the amino acid sequence set forth in SEQ ID NO: 1 wherein the gene is downstream of a telomerase promoter.

4. The recombinant adenoviral vector according to claim 3, wherein the recombinant adenoviral vector comprises the gene coding for protein (a).

5. A recombinant adenoviral vector comprising:
   a gene coding for a transcription factor, wherein the gene is under control of a telomerase promoter, and
   a second gene coding for a protein selected from the group consisting of (a) a protein comprising the amino acid sequence of SEQ ID NO: 1; and (b) a protein comprising the amino acid sequence of SEQ ID NO: 1, wherein one amino acid is deleted, substituted, or inserted in the amino acid sequence set forth in SEQ ID NO: 1, wherein the second gene is downstream of a promoter sequence to which the transcription factor binds.

6. The recombinant adenoviral vector according to claim 5, wherein the second gene codes for protein (a).

7. A viral vector kit comprising;
   a recombinant vector comprising a gene selected from the group consisting of (i) a DNA comprising the nucleotide sequence of SEQ ID NO: 2, and (ii) a DNA comprising the nucleotide sequence of SEQ ID NO: 2, wherein one nucleotide is deleted, substituted, or inserted in the nucleotide sequence set forth in SEQ ID NO: 2, and wherein the gene is downstream of a promoter sequence to which a transcription factor binds; and
   a recombinant adenoviral vector comprising a second gene coding for the transcription factor, wherein the second gene is under control of a telomerase promoter.

8. The viral vector kit according to claim 7, wherein the recombinant vector comprises the gene (i).

9. A recombinant adenoviral vector comprising a gene selected from the group consisting of (i) a DNA comprising the nucleotide sequence of SEQ ID NO: 2, and (ii) a DNA comprising the nucleotide sequence of SEQ ID NO: 2, wherein one nucleotide is deleted, substituted, or inserted in the nucleotide sequence set forth in SEQ ID NO: 2, and wherein the gene is downstream of a telomerase promoter.

10. The recombinant adenoviral vector according to claim 9, wherein the recombinant vector comprises the gene (i).

11. A recombinant adenoviral vector comprising:
    a gene coding for a transcription factor, wherein the gene is under control of a telomerase promoter, and
    a second gene selected from the group consisting of (i) a DNA comprising the nucleotide sequence of SEQ ID NO: 2 and (ii) a DNA comprising the nucleotide sequence of SEQ ID NO: 2, wherein one nucleotide is deleted, substituted, or inserted in the nucleotide sequence set forth in SEQ ID NO: 2, and wherein the second gene is downstream of a promoter sequence to which the transcription factor binds.

12. The recombinant adenoviral vector according to claim 11, wherein the second gene comprises (i).

13. A method of breaking down cellular cytoskeleton in human fibrosarcoma cells or uterine cervical cancer cells in vitro, which comprises:
    transfecting a recombinant vector into the human fibrosarcoma cells or uterine cervical cancer cells; and
    transducing a recombinant adenoviral vector into the human fibrosarcoma cells or uterine cervical cancer cells;
    wherein the recombinant vector comprises a gene coding for a protein selected from the group consisting of: (a) a protein comprising the amino acid sequence of SEQ ID NO: 1, and (b) a protein comprising the amino acid sequence of SEQ ID NO: 1, wherein one amino acid is deleted, substituted, or inserted in the amino acid sequence set forth in SEQ ID NO: 1,
    wherein said first nucleic acid is downstream and operatively linked to a promoter sequence to which a transcription factor binds,
    wherein the recombinant adenoviral vector comprises a second nucleic acid encoding for the transcription factor, wherein the second nucleic acid is under the control of a telomerase promoter,
    wherein the transcription factor is expressed and binds to the promoter of the recombinant vector to express the protein in the human fibrosarcoma cells or the uterine cervix cancer cells; and
    wherein expression of the protein breaks down the cellular cytoskeleton.

14. A method of breaking down cellular cytoskeleton in human fibrosarcoma cells or uterine cervical cancer cells in vitro, which comprises:
    transfecting a recombinant vector into the human fibrosarcoma cells or uterine cervical cancer cells; and
    transducing a recombinant adenoviral vector into the human fibrosarcoma cells or uterine cervical cancer cells;
    wherein the recombinant vector comprises a first nucleic acid sequence comprising SEQ ID NO: 2, and wherein said first nucleic acid is downstream and operatively linked to a promoter sequence to which a transcription factor binds,
    wherein the recombinant adenoviral vector comprises a second nucleic acid encoding for the transcription factor, wherein the second nucleic acid is under the control of a telomerase promoter,
    wherein the transcription factor is expressed and binds to the promoter of the recombinant vector to express a protein encoded by the first nucleic acid in the human fibrosarcoma cells or the uterine cervix cancer cells; and
    wherein expression of the protein encoded by the first nucleic acid breaks down the cellular cytoskeleton.

15. A method of breaking down cellular cytoskeleton in human fibrosarcoma cells or uterine cervical cancer cells in vitro, which comprises:
    transducing a recombinant adenoviral vector into the human fibrosarcoma cells or uterine cervical cancer cells;
    wherein the recombinant vector comprises a gene coding for a protein selected from the group consisting of: (a) a protein comprising the amino acid sequence of SEQ ID NO: 1, and (b) a protein comprising the amino acid sequence of SEQ ID NO: 1, wherein one amino acid is deleted, substituted, or inserted in the amino acid sequence set forth in SEQ ID NO: 1;
    wherein the nucleic acid sequence is downstream and operatively linked to a telomerase promoter, and
    wherein the expression of the protein encoded by the nucleic acid sequence breaks down the cellular cytoskeleton.

16. A method of breaking down cellular cytoskeleton in human fibrosarcoma cells or uterine cervical cancer cells in vitro, which comprises:
    transducing a recombinant adenoviral vector into the human fibrosarcoma cells or uterine cervical cancer cells;
    wherein the recombinant adenoviral vector comprises the nucleic acid sequence of SEQ ID NO: 2, and wherein the nucleic acid sequence of SEQ ID NO: 2 is downstream and operatively linked to a telomerase promoter, and
    wherein expression of the protein encoded by nucleic acid sequence breaks down the cellular cytoskeleton.

17. A method of breaking down cellular cytoskeleton in human fibrosarcoma cells or uterine cervical cancer cells in vitro, which comprises:
- transducing a recombinant adenoviral vector into the human fibrosarcoma cells or uterine cervical cancer cells;
- wherein the recombinant adenoviral vector comprises a first nucleic acid sequence encoding for a transcription factor, wherein said first nucleic acid sequence is under the control of a telomerase promoter, and
- a second nucleic acid sequence encoding for a protein selected from the group consisting of: (a) a protein comprising the amino acid sequence of SEQ ID NO: 1, and (b) a protein comprising the amino acid sequence of SEQ ID NO: 1, wherein one amino acid is deleted, substituted, or inserted in the amino acid sequence set forth in SEQ ID NO: 1,
- wherein the second nucleic acid sequence is downstream and operatively linked to a promoter sequence to which the transcription factor binds, and
- wherein expression of the transcription factor and the protein encoded by the second nucleic acid sequence breaks down the cellular cytoskeleton.

18. A method of breaking down cellular cytoskeleton in human fibrosarcoma cells or uterine cervical cancer cells in vitro, which comprises:
- transducing a recombinant adenoviral vector into the human fibrosarcoma cells or uterine cervical cancer cells;
- wherein the recombinant adenoviral vector comprises a first nucleic acid sequence encoding for a transcription factor, wherein the first nucleic acid sequence is under the control of a telomerase promoter, and
- a second nucleic acid sequence comprising the nucleotide sequence of SEQ ID NO: 2 and wherein the second nucleic acid sequence is downstream and operatively linked to a promoter sequence to which the transcription factor binds,
- wherein the transcription factor is expressed and binds to the promoter of the recombinant adenoviral vector to express the protein encoded by SEQ ID NO: 2 in the human fibrosarcoma cells or uterine cervical cancer cells; and
- wherein expression of the protein encoded by the second nucleic acid sequence breaks down the cellular cytoskeleton.

* * * * *

SEQUENCE LISTING

```
<160> NUMBER OF SEQ ID NOS: 6

<210> SEQ ID NO 1
<211> LENGTH: 820
<212> TYPE: PRT
<213> ORGANISM: Mouse
```

-continued

<400> SEQUENCE: 1

```
Met Lys Leu Ala Leu Leu Pro Trp Ile Leu Met Leu Leu Ser Thr Ile
1               5                   10                  15

Pro Gly Pro Gly Phe Thr Ala Gly Ala Gln Gly Ser Cys Ser Leu Arg
            20                  25                  30

Cys Gly Ala Gln Asp Gly Leu Cys Ser Cys His Pro Thr Cys Ser Gly
        35                  40                  45

Leu Gly Thr Cys Cys Glu Asp Phe Leu Asp Tyr Cys Leu Glu Ile Leu
    50                  55                  60

Pro Ser Ser Gly Ser Met Met Gly Gly Lys Asp Phe Val Val Gln His
65                  70                  75                  80

Leu Lys Trp Thr Asp Pro Thr Asp Gly Val Ile Cys Arg Phe Lys Glu
                85                  90                  95

Ser Ile Gln Thr Leu Gly Tyr Val Asp Asp Phe Tyr Gln Val His Cys
            100                 105                 110

Ile Ser Pro Leu Leu Tyr Glu Ser Gly Tyr Ile Pro Phe Thr Ile Ser
        115                 120                 125

Met Asp Asn Gly Arg Ser Phe Pro His Ala Gly Thr Trp Leu Ala Ala
    130                 135                 140

His Pro Tyr Lys Val Ser Glu Ser Glu Lys Ser Gln Leu Val Asn Glu
145                 150                 155                 160

Thr His Trp Gln Tyr Tyr Gly Thr Ser Asp Thr Arg Gly Asn Leu Asn
                165                 170                 175

Leu Thr Trp Asp Thr Ser Ala Leu Pro Thr Pro Ala Val Thr Ile Glu
            180                 185                 190

Leu Trp Gly Tyr Glu Glu Thr Gly Lys Pro Tyr Ser Gly Asn Trp Thr
        195                 200                 205

Ser Lys Trp Ser Tyr Leu Tyr Pro Leu Ala Thr Asn Ile Pro Asn Thr
    210                 215                 220

Gly Phe Phe Thr Phe Thr Pro Lys Pro Ala Ser Pro Gln Tyr Gln Arg
225                 230                 235                 240

Trp Lys Val Gly Ala Leu Arg Ile Ser Ser Arg Asn Tyr Pro Gly
                245                 250                 255

Glu Lys Asp Val Arg Ala Leu Trp Thr Asn Asp His Ala Leu Ala Trp
            260                 265                 270

His Leu Gly Asp Asp Phe Arg Ala Asp Ser Val Ala Trp Ala Arg Ala
        275                 280                 285

Gln Cys Leu Ala Trp Glu Ala Leu Glu Asp Gln Leu Pro Asn Phe Leu
    290                 295                 300

Thr Glu Leu Pro Asp Cys Pro Cys Thr Leu Ala Gln Ala Arg Ala Asp
305                 310                 315                 320

Ser Gly Arg Phe Phe Thr Asp Tyr Gly Cys Asp Ile Glu His Gly Ser
                325                 330                 335

Val Cys Thr Tyr His Pro Gly Ala Val His Cys Val Arg Ser Val Gln
            340                 345                 350

Ala Ser Pro Arg Tyr Gly Ser Gly Gln Gln Cys Cys Tyr Thr Ala Ala
        355                 360                 365

Gly Thr Gln Leu Leu Thr Ser Ser Thr Ser Gly Thr Pro Asp
    370                 375                 380

Arg Gly His Asp Trp Gly Ala Pro Pro Tyr Arg Thr Pro Arg Val
385                 390                 395                 400

Thr Gly Met Ser His Trp Leu Tyr Asp Val Ile Ser Phe Tyr Tyr Cys
                405                 410                 415
```

```
Cys Leu Trp Ala Pro Glu Cys Pro Arg Tyr Met Lys Arg Arg Pro Ser
            420                 425                 430

Ser Asp Cys Arg Asn Tyr Arg Pro Arg Leu Ala Ser Ala Phe Gly
            435                 440                 445

Asp Pro His Phe Val Thr Phe Asp Gly Thr Ser Phe Ser Phe Ser Gly
            450                 455                 460

Asn Gly Glu Tyr Val Leu Leu Glu Thr Thr Leu Ser Asp Leu Arg Val
465                 470                 475                 480

Gln Gly Arg Ala Gln Pro Gly Arg Met Pro Asn Gly Thr Gln Ala Arg
            485                 490                 495

Gly Thr Gly Leu Thr Ala Val Ala Val Gln Asp Asn Ser Asp Val
            500                 505                 510

Ile Glu Val Arg Leu Ala Gly Gly Ser Arg Val Leu Glu Val Leu Leu
            515                 520                 525

Asn Gln Lys Val Leu Ser Phe Thr Glu Gln Asn Trp Met Asp Leu Lys
            530                 535                 540

Gly Met Phe Leu Ser Val Ala Ala Gln Asp Lys Val Ser Ile Met Leu
545                 550                 555                 560

Ser Ser Gly Ala Gly Leu Glu Val Gly Val Gln Gly Pro Phe Leu Ser
            565                 570                 575

Val Ser Ile Leu Leu Pro Glu Lys Phe Leu Thr His Thr Arg Gly Leu
            580                 585                 590

Leu Gly Thr Leu Asn Asn Asn Pro Arg Asp Asp Phe Thr Leu Arg Asn
            595                 600                 605

Gly Gln Val Leu Pro Leu Asn Ala Ser Ala Gln Gln Val Phe Gln Phe
            610                 615                 620

Gly Ala Asp Trp Ala Val Ser Asn Thr Ser Ser Leu Phe Thr Tyr Asp
625                 630                 635                 640

Ser Trp Leu Leu Val Tyr Gln Phe Val Tyr Gly Pro Lys His Asn Pro
            645                 650                 655

Asn Phe Lys Pro Leu Phe Pro Asp Glu Thr Thr Leu Ser Pro Ser Gln
            660                 665                 670

Thr Glu Asp Val Ala Arg Leu Cys Glu Gly Asp Arg Phe Cys Ile Leu
            675                 680                 685

Asp Val Met Ser Thr Gly Ser Ser Ser Val Gly Asn Ala Thr Arg Ile
            690                 695                 700

Ala His Gln Leu His Gln His Arg Leu Lys Ser Leu Gln Pro Val Val
705                 710                 715                 720

Ser Cys Gly Trp Leu Pro Pro Ala Asn Gly His Lys Glu Gly Leu
            725                 730                 735

Arg Tyr Leu Glu Gly Ser Val Val Arg Phe Ser Cys Asn Asn Gly Tyr
            740                 745                 750

Ser Leu Val Gly Pro Glu Ser Ser Thr Cys Gln Ala Asp Gly Lys Trp
            755                 760                 765

Ser Met Pro Thr Pro Glu Cys Gln Pro Gly Arg Ser Tyr Thr Val Leu
            770                 775                 780

Leu Ser Ile Ile Phe Gly Gly Leu Ala Ile Val Ala Leu Ile Ser Ile
785                 790                 795                 800

Ile Tyr Met Met Leu His Arg Arg Lys Ser Asn Met Thr Met Trp
            805                 810                 815

Ser Ser Gln Pro
            820
```

<210> SEQ ID NO 2
<211> LENGTH: 3233
<212> TYPE: DNA
<213> ORGANISM: Mouse

<400> SEQUENCE: 2

```
gctctgagcc actgtgctgc ctgctggttg cagacacagg gcacaccatg aagctggccc      60
tcctgccttg gattttgatg ctgctctcaa caataccagg ccccgggttc acagcaggtg     120
cccagggaag ctgttccctg cgctgcgggg cacaggatgg actctgttcc tgtcacccaa     180
cctgctcggg ccttggcacc tgttgtgaag atttctgga ctactgccta gagattttac      240
cctcctcagg gtccatgatg ggtggcaaag acttcgtggt gcaacattta aagtggactg     300
accctactga tggggtcatt tgcaggttta aggagagtat ccaaacccct tggctatgtcg    360
acgacttcta tcaagtgcac tgcatatcac ccttgctcta tgaaagcggc tatattccct    420
tcaccatatc aatggacaat ggccgctcct tccctcatgc aggcacttgg ctagctgcac     480
atccctacaa agtgtctgaa tccgagaaga gccagctggt gaacgagacc cattggcaat    540
actacggcac ttcagacacc aggggaaacc tcaacctcac ctgggacact tcagcgctgc    600
ccacgccggc cgtcaccatt gagctgtggg gctatgagga gacaggaaaa ccctactctg    660
ggaactggac ctcgaagtgg tcctatctgt acccttggc tacaaacatc cccaataccg     720
gcttcttcac tttcacccc aaacccgcat cacctcagta ccagaggtgg aaagtgggtg    780
ctctgaggat cagcagcagc aggaactacc aggagagaa ggatgtgcgg gcgctctgga    840
ccaacgatca cgcactggcc tggcacctgg gtgacgactt ccgggcagac tccgtagcct    900
gggcccgagc acagtgcctg gcctgggagg cattggaaga ccaactaccc aacttcctga    960
cggagctgcc agactgcccc tgcacccctgg gccaggccag ggctgattct ggccgcttct   1020
tcactgacta tggttgtgac attgaacatg gcagcgtatg cacctaccac ccaggggctg   1080
tgcactgtgt gcgctctgtg caagccagcc ccaggtatgg ctcaggccag caatgctgct   1140
acacggcagc agggacacag ctcctgactt cagactcgac aagtggcagc acccctgacc   1200
gtggccacga ctggggtgca cccccatacc ggactcctcc ccgtgtgacc ggcatgtctc   1260
attggctcta tgacgtcatc agcttctatt actgctgtct ttgggctcct gagtgtcccc   1320
gttatatgaa gcgccggccc tccagtgact gccgcaacta cagacccca cgcctggcct    1380
ctgccttcgg gacccccat tttgtcacct ttgatggcac cagcttctcg ttcagcggca   1440
atggcgaata tgtgctattg gagaccaccc tgagtgatct gagagtgcag ggccgggccc   1500
agcctgggag aatgcccaat ggcacccagg cccgtggcac agggctgact gcagtggccg   1560
tccaagaaga caattcggat gtgatagagg tgcggttagc tggcgggtct cgggtcttgg   1620
aagtgttgct gaatcagaaa gtgctcagtt tcactgaaca aaattggatg gacctgaagg   1680
gcatgttcct gtcagtggcc gctcaggata aggtgtcaat catgttgtca tcgggggctg   1740
gcctcgaggt cggtgtacaa ggtcctttcc tgagtgtgag cattctgttg cctgagaagt   1800
ttctgaccca cacccgtggt ctcctgggga cactcaacaa taaccccagg gatgacttca   1860
ccctgcgcaa tggcaggtc ctgccccctga atgccagtgc tcagcaggtg ttccagtttg    1920
gagccgactg ggctgttttcc aacacgtctt ccctgtttac ttatgactct ggcttctgg   1980
tctaccaatt cgtgtacgga cccaagcaca ccccaactt caaaccactc ttccctgatg    2040
agaccacact cagccccagc cagacagaag atgtggccag actgtgtgag ggtgaccgtt   2100
tctgcatcct tgatgtgatg agcacaggaa gctcgagcgt gggcaacgcc acccggattg   2160
```

```
cccaccaact gcaccagcac cgtctgaaga gcctgcagcc tgtggtatcc tgtggctggc      2220
tacccccacc tgcaaacggg cataaggaag gcttgaggta cctggaagga tccgttgtcc      2280
gattcagctg caacaatggc tacagcttgg tggggccgga gagtagcacc tgtcaggctg      2340
atggaaagtg gtctatgcct accccagagt gtcagccagg gcggagctac acggtgctac      2400
tgagtatcat cttcggaggc ctggccatag tggcactgat ctctatcatc tatatgatgc      2460
tgcatcgccg caggaagagc aacatgacca tgtggagctc acagccctga accagagca      2520 cacttggctg acagcatcgg ccacgtgct caccaagacc cagtctcccc gggagaagcg      2580
caaagaacat gtaccctagt cctatgaatg ccacatctag tatctgtgcc ttgaacacta      2640
tggacccaat acctgtccta gcctgtcctt ctgactgaga catgataccg gatagtctta      2700
actccagaac cccacccca acacttctcc atcagtaacc tgcacttcct ttgtctattg      2760
gttatgactc taactcctca gacttaaggg atggccttct tgtcccgtcc tagaactgga      2820
gtacctatgt cccaagccct gcgttggaag ctcccatttc agttcctcac tccccagagc      2880
ctgataaact gagacctggt gcctgccttc ctgtgaggtc ccccagagct aaactgcctt      2940
gattcctgcc ccatggaaca acttgagagc tcgggttggc tcagtcccac aatgaagagt      3000
ggccccggag cctgagcagt gagaaagaga actgtccagc agagaagaga cctcttttgt      3060 acccagget tctactctta cctcttctct agcatactca ggaacgccct tccatcccca      3120
tacaagaaca caagctcatg ttacatcttt cctggttccc gtctgtttgt gtttccccac      3180
ggttccataa ctgtccgtga ggtcacccac taatagcatc agagtttgag ccc            3233

<210> SEQ ID NO 3
<211> LENGTH: 771
<212> TYPE: DNA
<213> ORGANISM: Artificial Sequence
<220> FEATURE:
<223> OTHER INFORMATION: Chemically synthesized fusion transcription
      factor Gal4VP2

<400> SEQUENCE: 3
atgaagctac tgtcttctat cgaacaagca tgcgatattt gccgacttaa aaagctcaag       60
tgctccaaag aaaaaccgaa gtgcgccaag tgtctgaaga caactgggga gtgtcgctac      120
tctcccaaaa ccaaaaggtc tccgctgact agggcacatc tgacagaagt ggaatcaagg      180
ctagaaagac tggaacagct atttctactg attttttcctc gagaagacct tgacatgatt      240
ttgaaaatgg attctttaca ggatataaaa gcattgttaa caggattatt tgtacaagat      300
aatgtgaata agatgccgt cacagataga ttggcttcag tggagactga tatgcctcta      360
acattgagac agcatagaat aagtgcgaca tcatcatcgg aagagagtag taacaaaggt      420
caaagacagt tgactgtatc gccggaattc ctgcagcccg ggggatccgc ccccccgacc      480
gatgtcagcc tggggacga gctccactta cggcgagg acgtggcgat ggcgcatgcc      540
gacgcgctag acgatttcga tctggacatg ttggggacg ggattccccc gggtccgaga      600
tccgcccccc cgaccgatgt cagcctgggg gacgagctcc acttagacgg cgaggacgtg      660
gcgatggcgc atgccgacgc gctagacgat ttcgatctgg acatgttggg gacggggat      720 tccccgggtc cgagatcctc tagaaatgtc gacagcttgg gatctttgtg a              771

<210> SEQ ID NO 4
<211> LENGTH: 212
<212> TYPE: DNA
<213> ORGANISM: Artificial Sequence
```

```
<220> FEATURE:
<223> OTHER INFORMATION: Chemically synthesized promoter G5E4T

<400> SEQUENCE: 4
tccggaggac agtactccgc tcggaggaca gtactccgct cggaggacag tactccgctc      60
ggaggacagt actccgctcg gaggacagta ctccgactct agaggatccc cagtcctata     120
tatactcgct ctgcacttgg ccctttttta cactgtgact gattgagctg gtgccgtgtc     180
gagtggtgtc tcgagatctg cgatctaagt aa                                   212

<210> SEQ ID NO 5
<211> LENGTH: 66
<212> TYPE: DNA
<213> ORGANISM: Artificial Sequence
<220> FEATURE:
<223> OTHER INFORMATION: Chemically synthesized FLAG tag gene

<400> SEQUENCE: 5
gattacaagg atcacgatgg tgattacaag gatcacgata tcgattacaa ggatgatgat      60
gataag                                                                 66

<210> SEQ ID NO 6
<211> LENGTH: 3221
<212> TYPE: DNA
<213> ORGANISM: Mouse

<400> SEQUENCE: 6
taagaattcc cggtgctgcc tgctggttgc agacacaggg cacaccatga agctggccct      60
cctgccttgg attttgatgc tgctctcaac aataccaggc cccgggttca cagcaggtgc     120
ccagggagat acaaggatc acgatggtga ttacaaggat cacgtatcg attacaagga      180 tgatgatgat aaggcccagg gaagctgttc cctgcgctgc ggggcacagg atggactctg     240
ttcctgtcac ccaacctgct cgggccttgg cacctgttgt gaagattttc tggactactg     300
cctagagatt ttaccctcct cagggtccat gatgggtggc aaagacttcg tggtgcaaca     360
tttaaagtgg actgaccccta ctgatggggt catttgcagg tttaaggaga gtatccaaac     420
ccttggctat gtcgacgact tctatcaagt gcactgcata tcacccttgc tctatgaaag     480
cggctatatt cccttcacca tatcaatgga caatggccgc tccttccctc atgcaggcac     540
ttggctagct gcacatccct acaaagtgtc tgaatccgag aagagccagc tggtgaacga     600
gacccattgg caatactacg gcacttcaga caccagggga aacctcaacc tcacctggga     660
cacttcagcg ctgcccacgc cggccgtcac cattgagctg tggggctatg aggagacagg     720
aaaaccctac tctgggaact ggaccctcgaa gtggtcctat ctgtaccctt tggctacaaa     780
catccccaat accggcttct tcactttcac ccccaaaccc gcatcacctc agtaccagag     840
gtggaaagtg ggtgctctga ggatcagcag cagcaggaac tacccaggag agaaggatgt     900
gcgggcgctc tggaccaacg atcacgcact ggcctggcac ctgggtgacg acttccgggc     960
agactccgta gcctgggccc gagcacagtg cctggcctgg gaggcattgg aagaccaact    1020
acccaacttc ctgacggagc tgccagactg ccccctgcacc ctggcccagg ccagggctga    1080
ttctggccgc ttcttcactg actatggttg tgacattgaa catggcagcg tatgcaccta    1140
ccacccaggg gctgtgcact gtgtgcgctc tgtgcaagcc agcccaggt atggctcagg    1200 ccagcaatgc tgctacacgg cagcaggac acagctcctg acttcagact cgacaagtgg    1260
cagcacccct gaccgtggcc acgactgggg tgcaccccca taccggactc ctcccgtgt    1320
```

```
gcccggcatg tctcattggc tctatgacgt catcagcttc tattactgct gtctttgggc    1380
tcctgagtgt ccccgttata tgaagcgccg gccctccagt gactgccgca actacagacc    1440
cccacgcctg gcctctgcct tcggggaccc ccattttgtc acctttgatg gcaccagctt    1500
ctcgttcagc ggcaatggcg aatatgtgct attggagacc accctgagtg atctgagagt    1560
gcagggccgg gcccagcctg ggagaatgcc caatggcacc caggcccgtg gcacagggct    1620
gactgcagtg gccgtccaag aagacaattc ggatgtgata gaggtgcggt tagctggcgg    1680
gtctcgggtc ttggaagtgt tgctgaatca gaaagtgctc agtttcactg aacaaaattg    1740
gatggacctg aagggcatgt tcctgtcagt ggccgctcag gataaggtgt caatcatgtt    1800
gtcatcgggg gctggcctcg aggtcggtgt acaaggtcct ttcctgagtg tgagcattct    1860
gttgcctgag aagtttctga cccacacccg tggtctcctg gggacactca acaataaccc    1920
cagggatgac ttcaccctgc gcaatgggca ggtcctgccc ctgaatgcca gtgctcagca    1980
ggtgttccag tttggagccg actgggctgt ttccaacacg tcttccctgt ttacttatga    2040
ctcttggctt ctggtctacc aattcgtgta cggacccaag cacaacccca acttcaaacc    2100
actcttccct gatgagacca cactcagccc cagccagaca gaagatgtgg ccagactgtg    2160
tgagggtgac cgtttctgca tccttgatgt gatgagcaca ggaagctcga gcgtgggcaa    2220
cgccacccgg attgccacc aactgcacca gcaccgtctg aagagcctgc agcctgtggt    2280
atcctgtggc tggctacccc cacctgcaaa cgggcataag gaaggcttga ggtacctgga    2340
aggatccgtt gtccgattca gctgcaacaa tggctacagc ttggtggggc cggagagtag    2400
cacctgtcag gctgatggaa agtggtctat gcctacccca gagtgtcagc cagggcggag    2460
ctacacggtg ctactgagta tcatcttcgg aggcctggcc atagtggcac tgatctctat    2520
catctatatg atgctgcatc gccgcaggaa gagcaacatg accatgtgga gctcacagcc    2580
ctgagaccag agcacacttg gctgacagca tcgggccacg tgctcaccaa gacccagtct    2640
ccccgggaga gcgcaaaga acatgtaccc tagtcctatg aatgccacat ctagtatctg    2700
tgccttgaac actatggacc caatacctgt cctagcctgt ccttctgact gagacatgat    2760
accggatagt cttaactcca gaaccccacc cccaacactt ctccatcagt aacctgcact    2820
tcctttgtct attggttatg actctaactc ctcagactta agggatggcc ttcttgtccc    2880
gtcctagaac tggagtacct atgtcccaag ccctgcgttg gaagctccca tttcagttcc    2940
tcactcccca gagcctgata aactgagacc tggtgcctgc cttcctgtga ggtcccccag    3000
agctaaactg ccttgattcc tgccccatgg aacaacttga gagctcgggt tggctcagtc    3060
ccacaatgaa gagtggcccc ggagcctgag cagtgagaaa gagaactgtc cagcagagaa    3120
gagacctctt ttgtaccca ggtttctact cttacctctt ctctagcata ctcaggaacg    3180
cccttccatc cccatacaag aacacaagct catgttacat c                        3221
```